(12) United States Patent
Pollen et al.

(10) Patent No.: US 10,143,781 B1
(45) Date of Patent: Dec. 4, 2018

(54) TIP-TOLERANT CHEST DRAINAGE CONTAINER

(71) Applicants: Ashia M. Pollen, Madison, WI (US); Robert J. Harter, La Crosse, WI (US)

(72) Inventors: Ashia M. Pollen, Madison, WI (US); Robert J. Harter, La Crosse, WI (US)

( * ) Notice: Subject to any disclaimer, the term of this patent is extended or adjusted under 35 U.S.C. 154(b) by 1115 days.

(21) Appl. No.: 14/466,981

(22) Filed: Aug. 23, 2014

Related U.S. Application Data

(60) Provisional application No. 61/881,567, filed on Sep. 24, 2013, provisional application No. 61/881,571, filed on Sep. 24, 2013.

(51) Int. Cl.
  *A61M 1/00* (2006.01)

(52) U.S. Cl.
  CPC ....... *A61M 1/0001* (2013.01); *A61M 2202/04* (2013.01); *A61M 2205/21* (2013.01); *A61M 2210/101* (2013.01)

(58) Field of Classification Search
  CPC .. A61M 1/00; A61M 1/0001; A61M 2202/04; A61M 2210/101; A61M 2205/21
  See application file for complete search history.

(56) References Cited

U.S. PATENT DOCUMENTS

| | | |
|---|---|---|
| 4,430,085 A | 2/1984 | Ahrens |
| 4,439,189 A | 3/1984 | Sargeant et al. |
| 4,544,370 A | 10/1985 | Elliott et al. |
| 4,601,715 A | 7/1986 | Olson |
| 4,650,476 A | 3/1987 | Telang |
| 4,738,671 A | 4/1988 | Elliott et al. |
| 4,747,844 A | 5/1988 | Elliott |
| 4,781,707 A | 11/1988 | Boehringer et al. |
| 4,955,874 A | 9/1990 | Farrar et al. |
| 4,963,135 A | 10/1990 | Kerwin |
| 4,988,342 A | 1/1991 | Herweck et al. |
| 4,994,050 A | 2/1991 | Weilbacher et al. |
| 5,026,358 A | 6/1991 | Everett, Jr. et al. |
| 5,114,416 A | 5/1992 | Karwoski et al. |
| D328,790 S | 8/1992 | Herweck et al. |
| 5,141,504 A | 8/1992 | Herweck et al. |

(Continued)

*Primary Examiner* — Benjamin Klein
*Assistant Examiner* — Sara Sass
(74) *Attorney, Agent, or Firm* — bobharter.com; Robert J. Harter

(57) ABSTRACT

A chest drainage container for withdrawing and collecting certain body fluids from within a patient's chest cavity includes means for tolerating the container being accidentally tipped over. To provide such means, some example containers disclosed in this patent merely involve modifying the plastic injection mold of an existing chest drainage container. In some examples, certain partitions and vents are integrally formed in the container's main body. In the event of a tip-over occurrence, the partitions trap collected fluid within their appropriate collection chambers to help prevent inter-chamber mixing of fluid. During normal operation, the vents enable a pocket of otherwise trapped air to escape from within the enclosed collection chambers as incoming body fluid displaces the air. In some examples, under certain conditions, the vent releases gaseous fluid at a volumetric flow that is about 30 times greater than what the vent releases of liquid fluid during a tip-over event.

8 Claims, 13 Drawing Sheets

(56) References Cited

U.S. PATENT DOCUMENTS

| | | |
|---|---|---|
| 5,154,712 A | 10/1992 | Herweck et al. |
| D340,285 S | 10/1993 | Herweck et al. |
| 5,286,262 A | 2/1994 | Herweck et al. |
| 5,372,593 A | 12/1994 | Boehringer et al. |
| 5,397,299 A | 3/1995 | Karwoski et al. |
| 5,401,262 A | 3/1995 | Karwoski et al. |
| RE35,225 E | 4/1996 | Herweck et al. |
| 5,507,734 A | 4/1996 | Everett, Jr. et al. |
| 5,722,964 A | 3/1998 | Herweck et al. |
| 5,807,358 A | 9/1998 | Herweck et al. |
| 5,865,408 A | 2/1999 | Swisher et al. |
| 5,989,234 A | 11/1999 | Valerio et al. |
| D430,286 S | 8/2000 | Valerio et al. |
| 6,210,383 B1 | 4/2001 | Want et al. |
| 6,250,482 B1 | 6/2001 | Want et al. |
| 6,338,728 B1 | 1/2002 | Valerio et al. |
| 6,358,218 B1 | 3/2002 | Want et al. |
| 6,368,311 B1 | 4/2002 | Valerio et al. |
| 6,447,491 B1 * | 9/2002 | Lord .................. A61M 1/0031 604/317 |
| 6,659,987 B2 | 12/2003 | Swisher et al. |
| 6,749,592 B2 | 6/2004 | Lord |
| 6,902,550 B2 | 6/2005 | Want et al. |
| 6,976,977 B2 | 12/2005 | Yam |
| 7,028,707 B2 | 4/2006 | Corbeil et al. |
| 7,232,104 B2 | 6/2007 | Want et al. |
| 7,686,801 B2 | 3/2010 | Corbeil et al. |
| 2002/0058915 A1 * | 5/2002 | Wakabayashi ...... A61M 1/0023 604/319 |
| 2013/0110057 A1 | 5/2013 | Croteau et al. |

\* cited by examiner

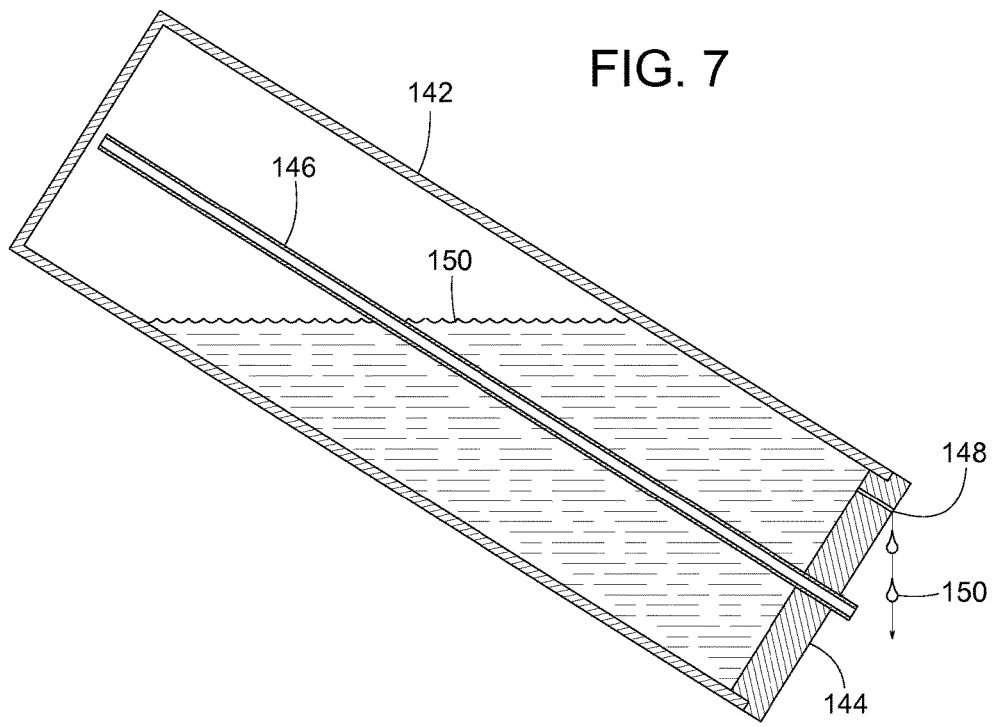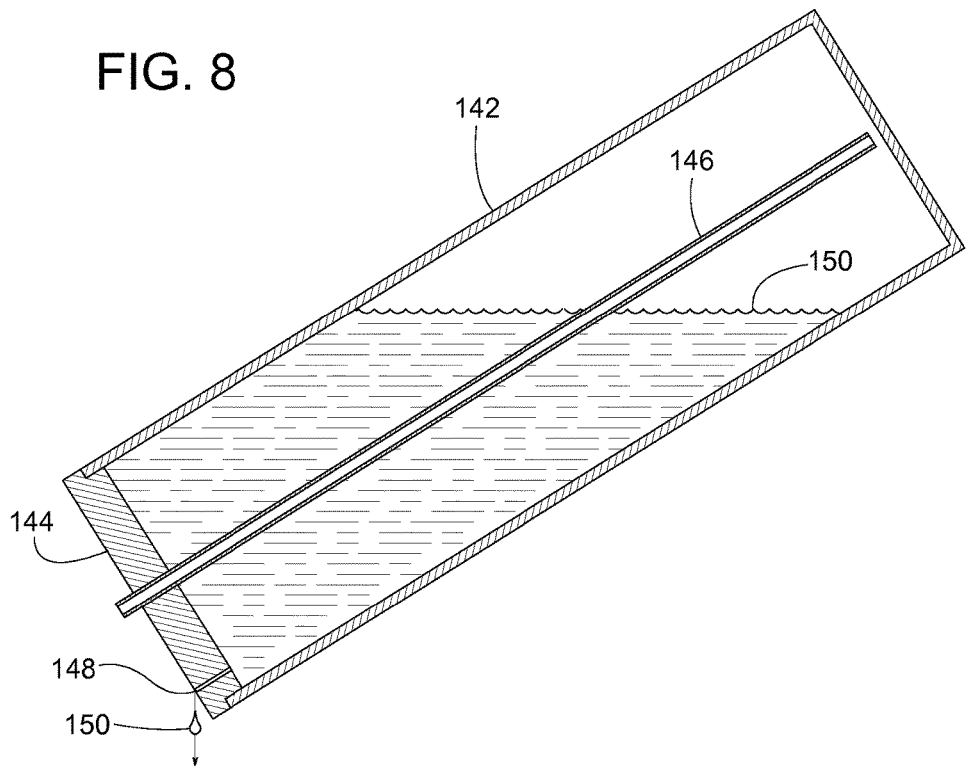

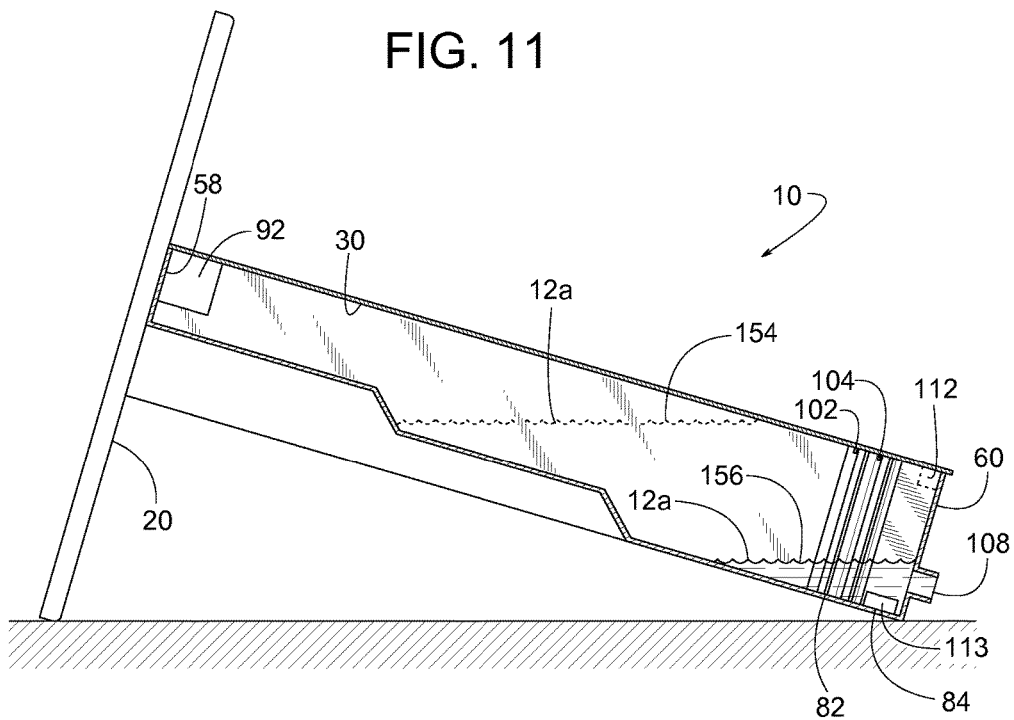
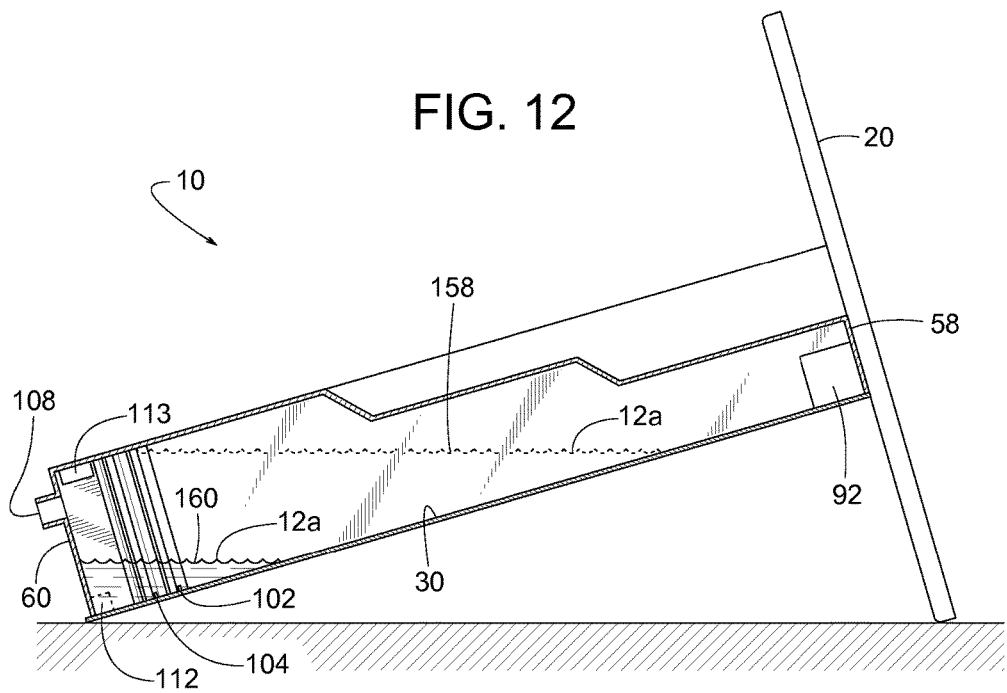

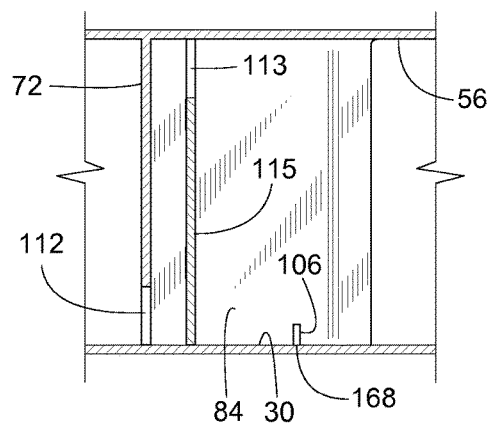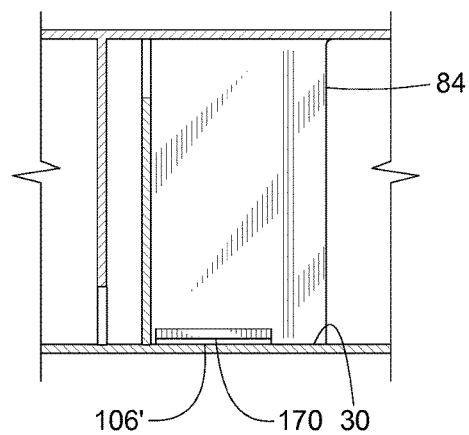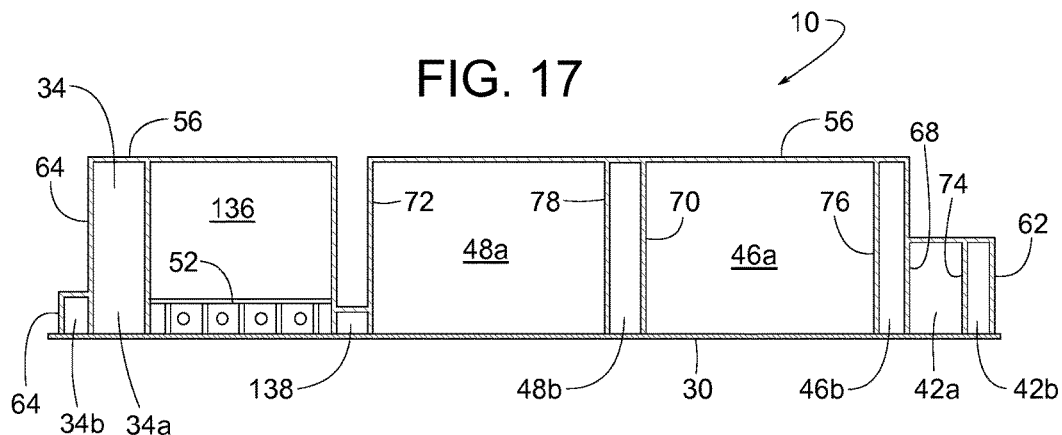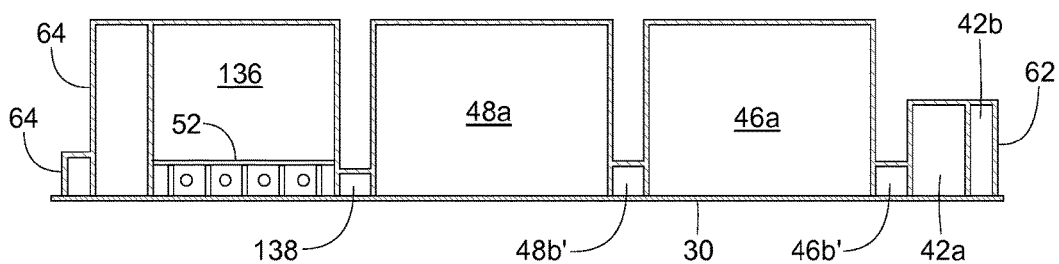

TIP-TOLERANT CHEST DRAINAGE CONTAINER

CROSS REFERENCE TO RELATED APPLICATIONS

This application claims the benefit of provisional patent application Ser. No. 61/881,567 filed on Sep. 24, 2013 by the present inventors and is hereby incorporated by reference. This application also claims the benefit of provisional patent application Ser. No. 61/881,571 filed on Sep. 24, 2013 by the present inventors and is hereby incorporated by reference.

FIELD OF THE DISCLOSURE

The subject invention generally pertains to containers for collecting body fluids from a patient and more specifically to chest drainage containers.

BACKGROUND

Certain medical treatments and patient recovery procedures involve chest drainage container systems for maintaining a patient's pleural space at a predetermined subatmospheric pressure and for withdrawing and collecting certain excess body fluids (e.g., pleural fluid, serous fluid, blood, lymphatic fluid or chyle, pus, etc.) from within the pleural space or from within other areas of the chest cavity. A typical system includes a catheter or chest tube connecting the pleural space, or other chosen chest cavity site, in fluid communication with a sealed container held at a specified subatmospheric pressure. The suction pressure within the chest drainage container draws fluids from within the chest cavity, through the chest tube and into the container.

Exemplary chest drainage containers and related components are disclosed in Teleflex's U.S. Pat. Nos. 6,749,592; 6,447,491; 6,338,728; 6,368,311; Des. 430,286; 5,989,234; and 5,507,734; all of which are hereby incorporated by reference. Additional chest drainage containers and related components are disclosed in U.S. Pat. Nos. 7,686,801; 7,232,105; 7,028,707; 6,902,550; 6,358,218; 6,250,482; 6,210,383; 5,807,358; 5,722,964; Re 35,225; 5,401,262; 5,397,299; 5,286,262; Des 340,285; 5,154,712; 5,141,504; Des 328,790; 5,114,416 and 4,988,342; all of which are hereby incorporated by reference.

State-of-the-art chest drainage containers have three main sections, a suction regulator, a fluidic seal and a body fluid collection chamber. The suction regulator provides means for adjusting and regulating the container's suction pressure. Known example suction regulators include a manometer that limits suction pressure by releasing atmospheric air into the container as needed, a dry mechanical pressure relief valve that breaks or limits vacuum when the drainage container reaches a predetermined lower suction pressure, and a controller that controls the operation of a vacuum pump connected to the container.

The fluidic seal, sometimes known as a "water seal" or "one-way valve," is usually situated between the suction regulator and the collection chamber. The fluidic seal helps prevent direct entry of atmospheric air from the suction regulator into the body fluid collection chamber. Some fluidic seals include a bubble indicator for detecting an air leak that might exist somewhere along the chest tube.

The fluidic seal connects the suction regulator in fluid communication with the container's body fluid collection chamber. A typical collection chamber comprises a series of sub-compartments that collect drained body fluids in a cascading manner from one sub-compartment to the next. Graduated windows on the container can provide means for measuring the volume of collected fluid.

Chest drainage containers work well when used properly. Sometimes, however, a chest drainage container can be accidentally tipped over. To address this problem, many Teleflex chest drainage containers have hangers for securing the container to a bed frame or other stable structure. To allow the option of setting the container on the floor, many Teleflex containers also have a swing-out leg that can be deployed to help stabilize the container in an upright, standing position.

BRIEF DESCRIPTION OF THE DRAWINGS

FIG. 7 is a schematic diagram similar to FIG. 5 but showing the model partially inverted in one direction.

FIG. 8 is a schematic diagram similar to FIG. 7 but showing the model partially inverted in the opposite direction.

FIG. 11 is a cross-sectional view similar to FIG. 10 but showing the chest drainage container tipped over to a reclined position.

FIG. 12 is a cross-sectional view similar to FIG. 10 but showing the chest drainage container tipped over to a prostrate position.

FIG. 16 is a cross-sectional view taken along line 16-16 of FIG. 1.

FIG. 16A is a cross-sectional view similar to FIG. 16 but showing an alternate vent profile.

FIG. 17 is a cross-sectional view taken along line 17-17 of FIG. 18.

FIG. 17A is a cross-sectional view similar to FIG. 17 but showing a modified main body with second and third receiving channels having a reduced volume.

DETAILED DESCRIPTION

Figure 1:
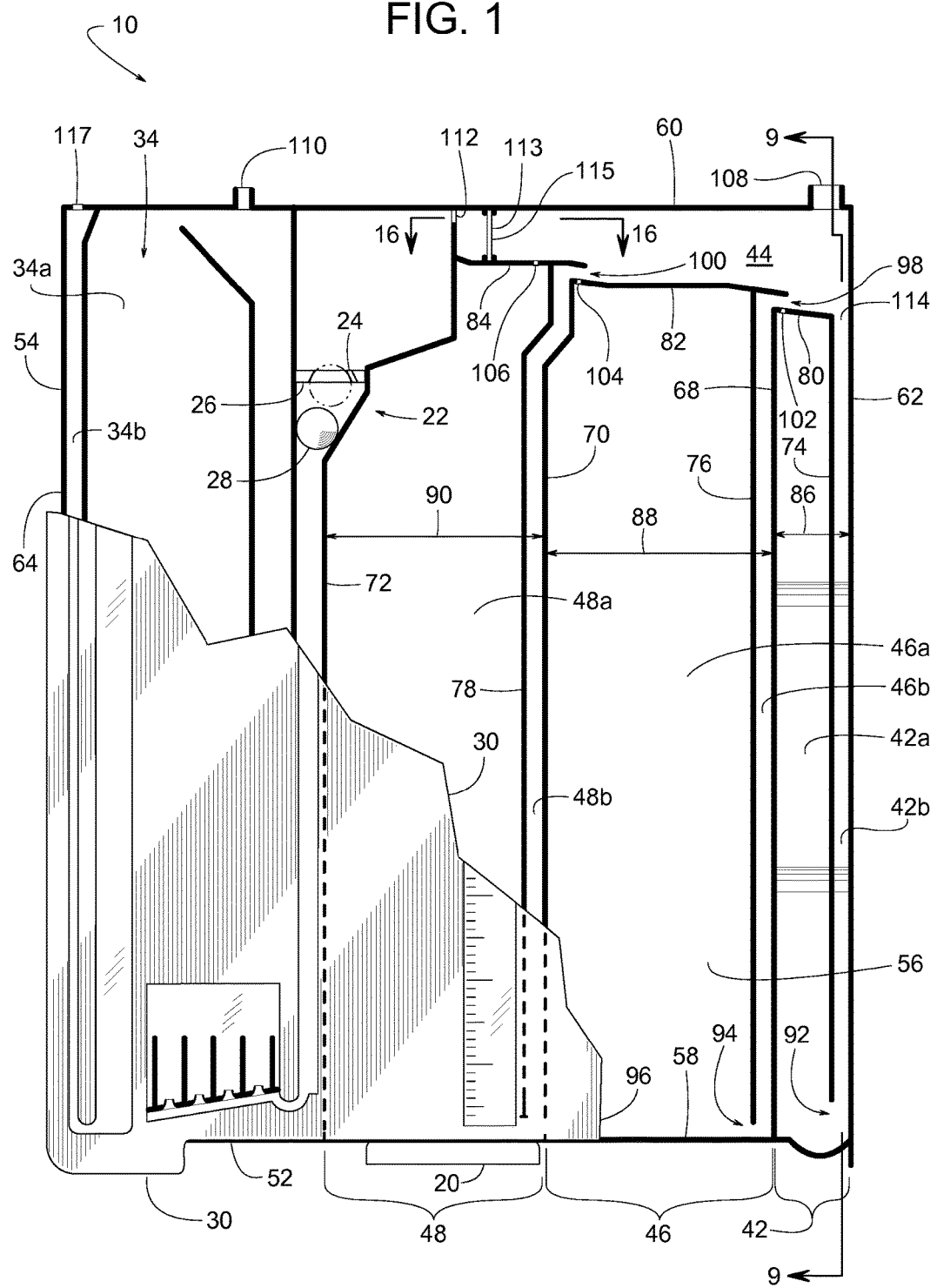
FIG. 1 is a front view of an example chest drainage container in accordance with the teachings disclosed in this patent (a front cover is partially cutaway).

To provide chest drainage containers with means for tolerating being tipped over, an example chest drainage container 10 includes various passageways, spillways and vents that are strategically sized and positioned to fully capitalize on the different flow characteristics of a body fluid 12. Some examples of body fluid 12 include a liquid body fluid 12a, a gaseous body fluid 12b, and liquid body fluid 12a mixed with solid or gelatinous body matter 14 (e.g., tissue and clots). In some cases, gaseous body fluid 12b is generated from within a patient 16 and/or is comprised of ambient air leaking into a catheter or chest tube 18 connected to patient 16. The tip-over tolerance of chest drainage container 10 is made possible because of two known features commonly found in modern Teleflex chest drainage containers. Specifically, the two features include a support leg 20 and a float valve 22.

While support leg 20 helps prevent tipping, once chest drainage container 10 is tipped over, leg 20 holds container 10 in a declining, partially inverted position where leg 20 props up the bottom of container 10 significantly higher than the top. Although this would seem to worsen the problem of fluids backflowing into the wrong chambers within container 10, the present invention uses the container's inverted position to a surprising advantage.

Various examples of container 10 avoid adverse interchamber fluid flow by exploiting the container's inverted position in combination with the restricted flow characteristics of Teleflex's float valve 22. Telflex float valve 22, as disclosed in U.S. Pat. No. 5,507,734, which is hereby incorporated by reference, provides a controlled leak path 24 between a valve seat 26 and an engaging float 28. In some examples of the present invention, float valve 22 buys a person time to right a tipped-over container before certain restricted vents can release liquid to the wrong collection chamber. A full explanation of chest drainage container 10 as it relates to support leg 20 and float valve 22 is as follows.

Figure 2:
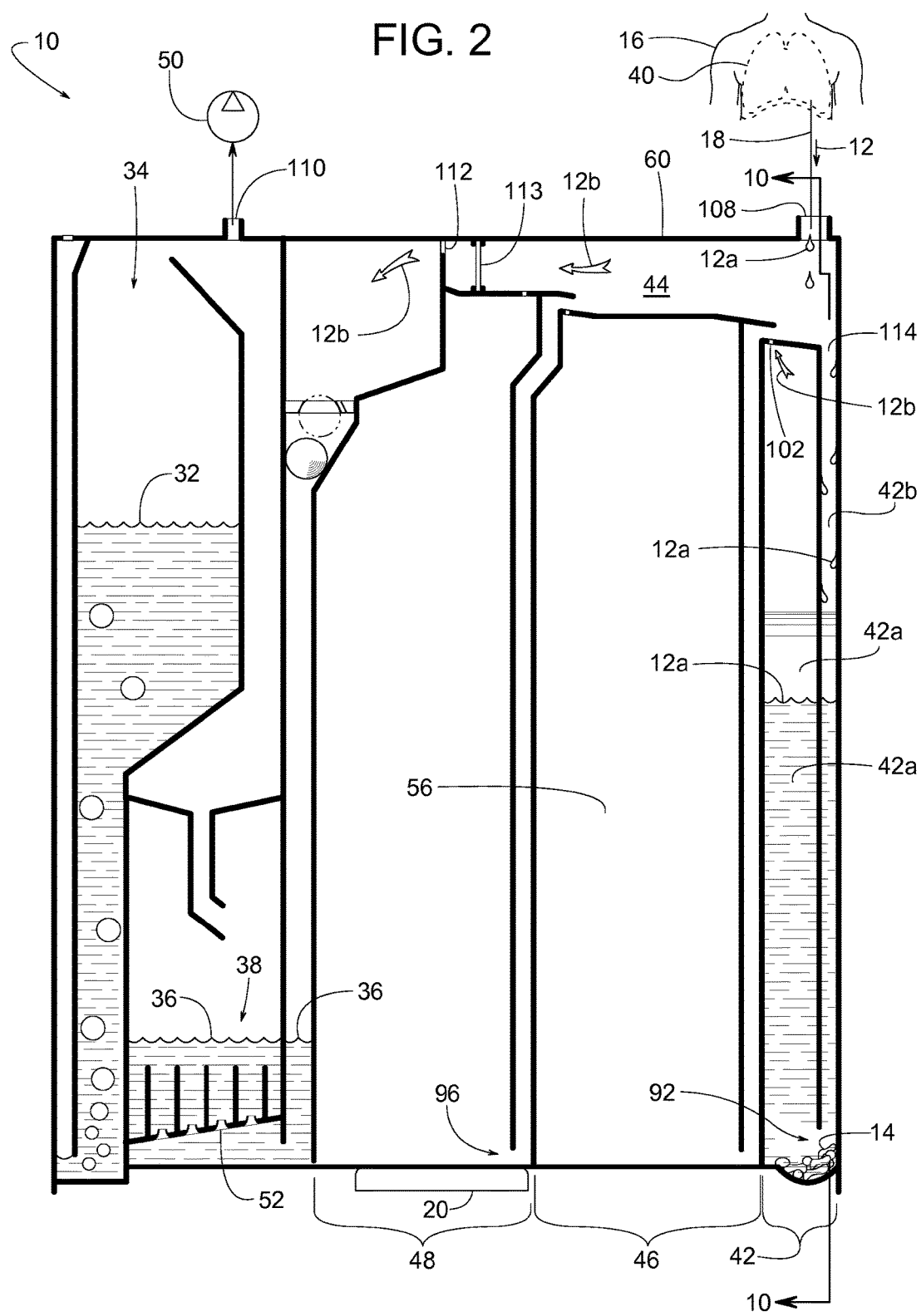
FIG. 2 is a front view similar to FIG. 1 but showing the chest drainage container in operation (front cover is completely cutaway).
Figure 3:
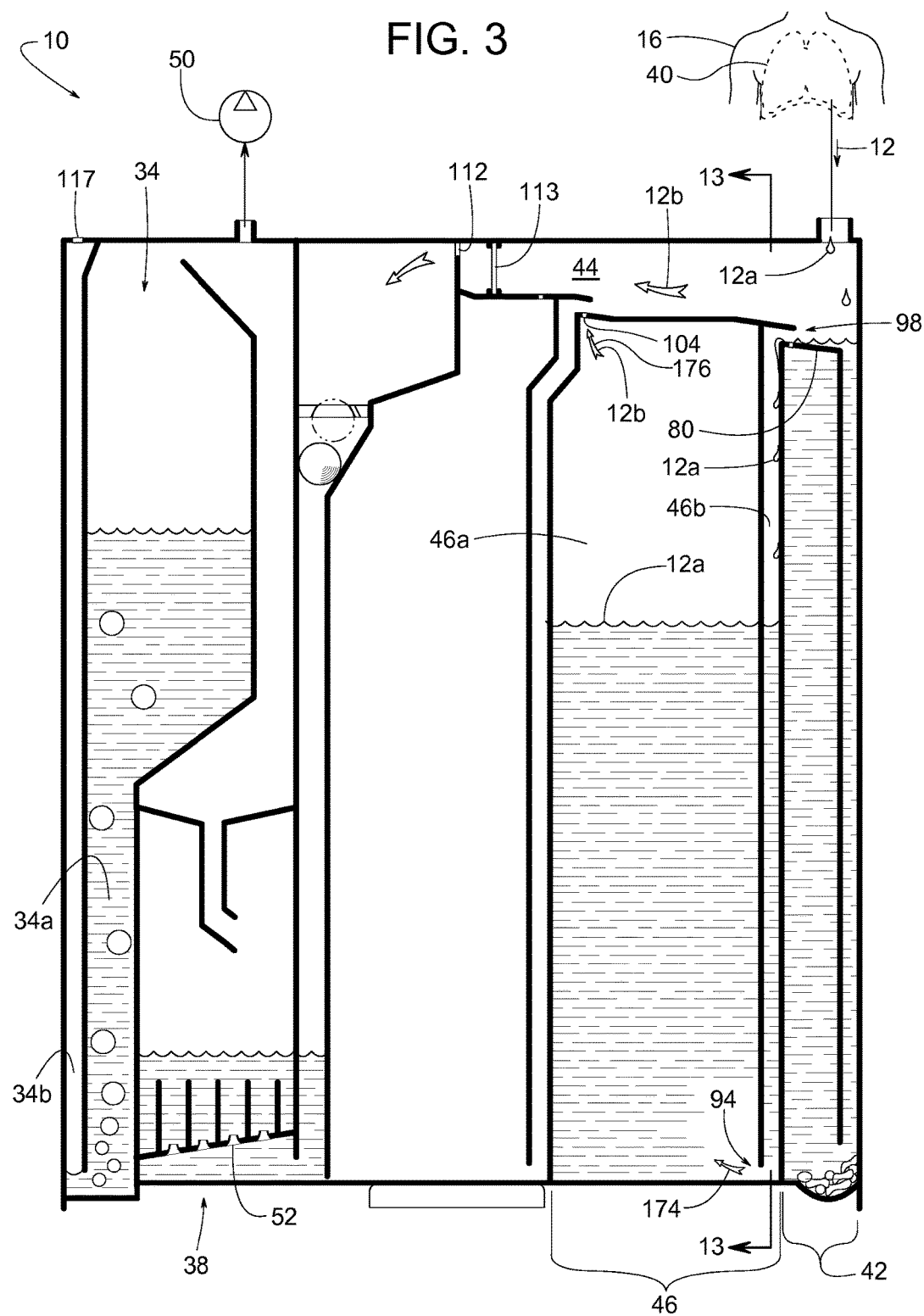
FIG. 3 is a front view similar to FIG. 2 but showing the chest drainage container in another operational state.
Figure 4:
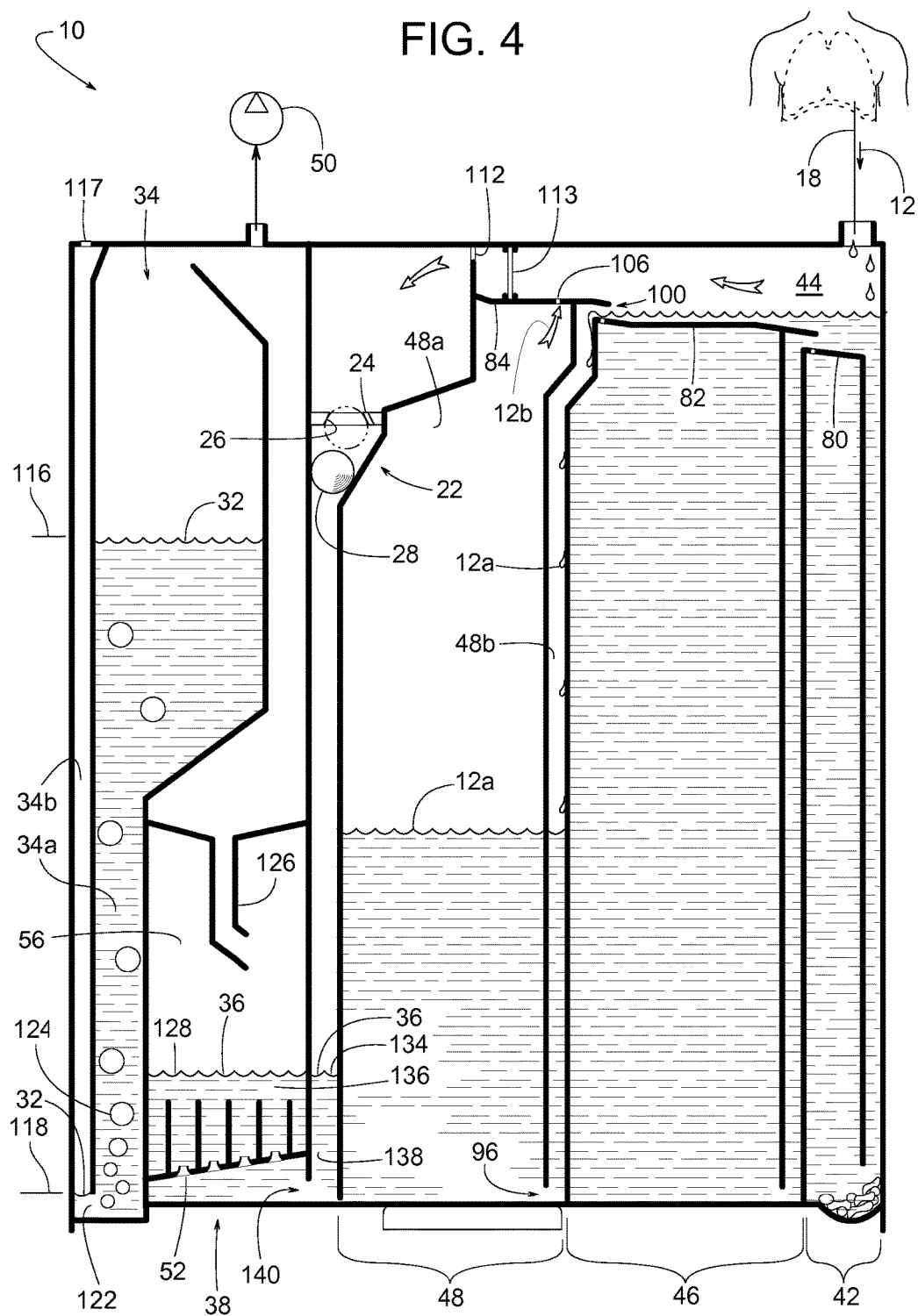
FIG. 4 is a front view similar to FIGS. 2 and 3 but showing the chest drainage container in another operational state.

FIGS. 1-4 show various states of one example chest drainage container 10 while FIGS. 5-8 schematically illustrate its underlying principle for avoiding adverse interchamber fluid flow during a tip-over condition. In FIGS. 1-4, a front panel 30 or portions of it are not shown to reveal other features of container 10. FIG. 1 shows chest drainage container 10 empty and void of liquid fluids. FIG. 2, in this particular example, shows chest drainage container 10 containing water 32 in a suction regulator section 34, water 36 in a fluidic seal 38, liquid fluid 12a drained from a chest cavity 40 (thoracic cavity) of patient 16 and collecting in a first-stage fluid collection chamber 42, and gaseous fluid 12b flowing across an overflow chamber 44. Examples of liquid fluid 12a include, but are not limited to, serous fluid (hydrothorax), blood (haemothorax), lymphatic fluid or chyle (chylothorax), pus (pyothorax or empyema), and various combinations thereof. FIG. 3 shows liquid fluid 12a collected in first-stage fluid collection chamber 42 and additional fluid 12a having overflowed into a second-stage fluid collection chamber 46. FIG. 4 shows liquid fluid 12a having collected in first-stage fluid collection chamber 42, in second-stage fluid collection chamber 46 and in a third-stage fluid collection chamber 48.

Although the illustrated example shows suction regulator 34 using water 32 in a pressure relieving manometer for limiting the subatmospheric pressure within section 34, other known examples employ other means for controlling the suction pressure. Known examples of suction regulator 34 include, but are not limited to, a manometer that breaks or limits vacuum upon section 34 reaching a predetermined lower subatmospheric pressure limit, a dry mechanical pressure relief valve that releases atmospheric air into section 34 upon section 34 reaching a predetermined lower subatmospheric pressure limit, and a controller that controls the operation of a suction source 50 (e.g., a vacuum pump) to maintain section 34 at a predetermined subatmospheric pressure.

Although the illustrated example shows fluidic seal 38 using water 36 in a gas trap manometer for isolating suction regulator 34 from collection chambers 42, 46 and 48; other known examples employ other means for avoiding air contamination of the collection chambers. Known examples of fluidic seal 38 and associated components include, but are not limited to, water in a manometer or gas trap U-tube, a dry check valve, a wet check valve, a float valve, a bubble indicator 52 and various combinations thereof. In the illustrated example, fluidic seal 38 comprises a manometer, float valve 22 and bubble indicator 52.

Figure 9:
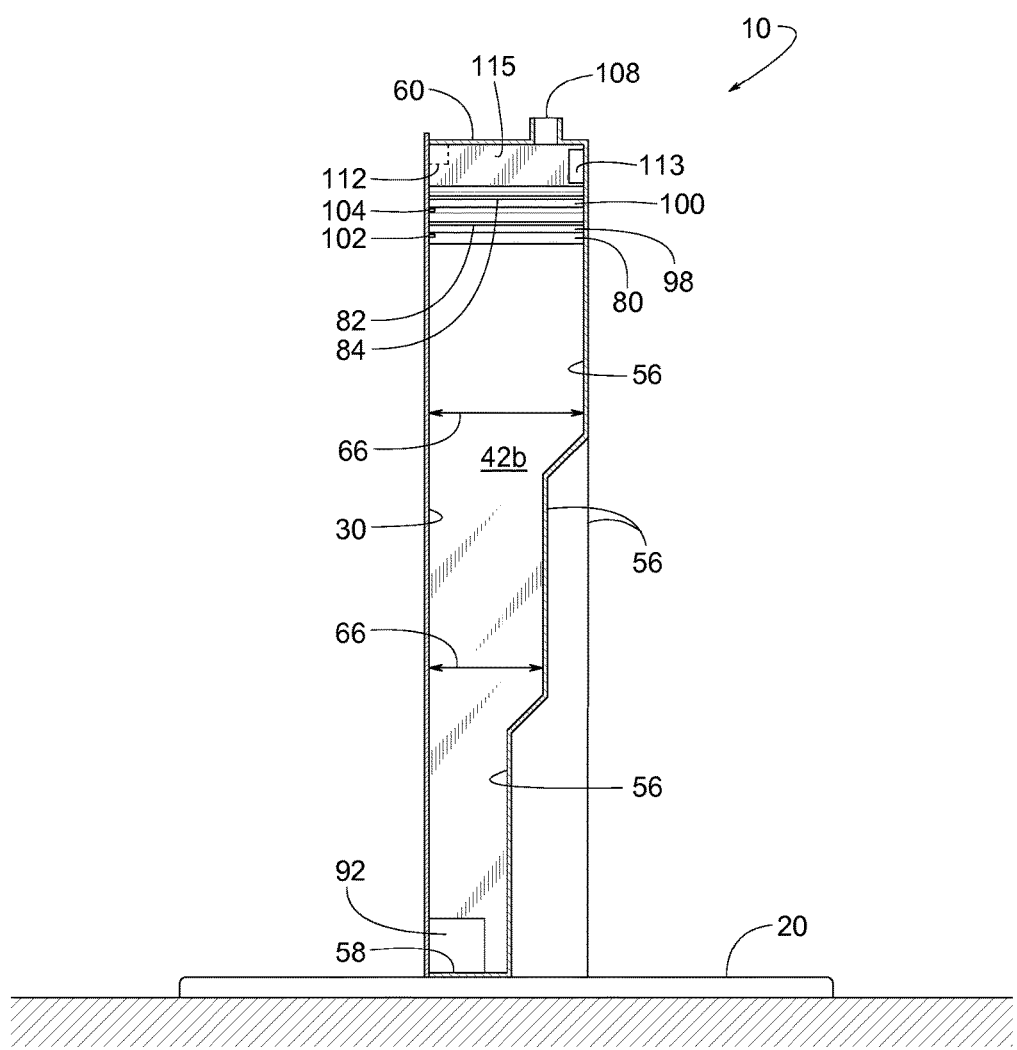
FIG. 9 is a cross-sectional view taken along line 9-9 of FIG. 1.

Referring to FIG. 1, the illustrated example of chest drainage container 10 includes a main body 54 comprising a back panel 56, a bottom panel 58, a top panel 60, a first outer side wall 62 and a second outer side wall 64. In some examples, main body 54 includes additional items, examples of which include, but are not limited to, partitions, dividing walls, lids, valves, moving parts, stationary parts, conduits, passageways, spillways, vents, inlets, tubes, slits, holes, baffles, etc. Front panel 30 attached to main body 54 defines an interior space of chest drainage container 10, wherein the interior space has a front-to-back depth 66 (e.g., uniform depth or of varying depth, as shown in FIG. 9) between front panel 30 and back panel 56. Within the interior space, some examples of chest drainage container 10 include a first dividing wall 68, a second dividing wall 70, a third dividing wall 72, a first partition 74, a second partition 76, a third partition 78, a first lid 80, a second lid 82 and a third lid 84.

In some examples, back panel 56, bottom panel 58, top panel 60, first outer side wall 62 and second outer side wall 64, together, is a unitary, seamless, plastic-injection molded piece. In some examples, back panel 56, bottom panel 58, top panel 60, first outer side wall 62, second outer side wall 64 and dividing walls 68, 70 and/or 72, together, is a unitary, seamless, plastic-injection molded piece. In some examples, back panel 56; bottom panel 58; top panel 60; first outer side wall 62; second outer side wall 64; dividing walls 68, 70 and/or 72; and partitions 74, 76 and/or 78; together, is a unitary, seamless, plastic-injection molded piece. In some examples, back panel 56; bottom panel 58; top panel 60; first outer side wall 62; second outer side wall 64; dividing walls 68, 70 and/or 72; partitions 74, 76 and/or 78; and lids 80, 82 and/or 84; together, is a unitary, seamless, plastic-injection molded piece (e.g., see FIGS. 17 and 17A).

In some examples, chest drainage container 10 includes various passageways, spillways and vents that interconnect (in fluid communication) various chambers, storage compartments and receiving channels. In the illustrated example, chest drainage container 10 includes: first stage fluid collection chamber 42 having a width 86 extending between first side wall 62 and first dividing wall 68 and having a height extending between bottom panel 58 and first lid 80; second stage fluid collection chamber 46 having a width 88 extending between first dividing wall 68 and second dividing wall 70 and having a height extending between bottom panel 58 and second lid 82; third stage fluid collection chamber 48 having a width 90 extending between second dividing wall 70 and third dividing wall 72 and having a height extending between bottom panel 58 and third lid 84; and overflow chamber 44 situated below top panel 60 and above at least one of lids 80, 82 and 84.

In some examples, a partition divides each fluid collection chamber 42, 46 and 48 into a storage compartment and a receiving channel. For example, first partition 74 divides first stage fluid collection chamber 42 into a first storage compartment 42a and a first receiving channel 42b; second partition 76 divides second stage fluid collection chamber 46 into a second storage compartment 46a and a second receiving channel 46b; and third partition 78 divides third stage fluid collection chamber 48 into a third storage compartment 48a and a third receiving channel 48b. Chest drainage container 10 can have any number of fluid collection chambers and associated partitions, lids and dividing walls. Some examples of chest drainage container 10 have four fluid collection chambers.

A first passageway 92 connects first receiving channel 46b in fluid communication with first storage compartment 46a. A second passageway 94 connects second receiving channel 46b in fluid communication with second storage compartment 46a. And a third passageway 96 connects third receiving channel 48b in fluid communication with third storage compartment 48a. A first interstage spillway 98 (receiving channel inlet), relatively close to top panel 60, connects first receiving channel 42b in fluid communication with second receiving channel 46b so that when first stage fluid collection chamber 42 is full, excess fluid can spill over into second receiving channel 46b. A second interstage spillway 100 (receiving channel inlet), relatively close to top panel 60, connects second receiving channel 46b in fluid communication with third receiving channel 48b so that when second stage fluid collection chamber 46 is full, excess fluid can spill over into third receiving channel 48b. Thus, spillways 98 and 100 connect fluid collection chambers 42, 46 and 48 in a cascade arrangement.

To allow collected liquid fluid 12a to rise up within storage compartments 42a, 46a and 48a without being opposed by an upper pocket of trapped air or gas (e.g., gaseous body fluid 12b), each storage compartment has a vent in fluid communication with overflow chamber 44. In some examples, first storage compartment 42a has a first vent 102, second storage compartment 46a has a second vent 104, and third storage compartment 48a has a third vent 106. First vent 102 is through, adjacent or at least proximate first lid 80 and is defined by first lid 80, first partition 74 and/or first dividing wall 68. Second vent 104 is through, adjacent or at least proximate second lid 82 and is defined by second lid 82, second partition 76 and/or second dividing wall 70. Third vent 106 is through, adjacent or at least proximate third lid 84 and is the defined by third lid 84, third partition 78 and/or second dividing wall 70.

Referring to FIGS. 2-4, to collect liquid fluid 12a from chest cavity 40 of patient 16 and/or to maintain a pleural space or other areas of chest cavity 40 at some predetermined subatmospheric pressure, chest tube 18 connects the patient's chest cavity 40 in fluid communication with a main fluid inlet 108 of chest drainage container 10, and suction source 50 connects to a suction port 110 leading to suction regulator 34 of container 10. Passageways 112 and 113 communicate the suction pressure of section 34 to main fluid inlet 108 and fluid collection chambers 42, 46 and 48. In some examples, passageway 112 is through an upper section of dividing wall 72, and passageway 113 is through a baffle 115. In some examples, baffle 115 and front panel 30 are plastic injection molded as a single piece. In some examples, baffle 115 is a separate piece inserted into main body 54 prior to installing front panel 30. Passageways 112 and 113 are staggered, as shown in FIG. 16, to provide a dam that inhibits liquid fluid 12a from spilling into fluidic seal 38 regardless of whether chest drainage container tips forward or back.

With passageways 112 and 113 and with chest drainage container under normal operation, suction source 50 reduces the air pressure within chest drainage container 10 to subatmospheric pressure and ultimately reduces the pressure within some areas of the patient's chest cavity 40 as well. The actual predetermined subatmospheric pressure is determined by suction regulator 34 via means suggested earlier and widely known to those of ordinary skill in the art.

With chest drainage container 10 maintained at subatmospheric pressure, liquid body fluid 12a drains first through main fluid inlet 108, through a receiving channel inlet 114, into first receiving channel 42b, and then sequentially fills fluid collection chambers 42, 46 and 48, as illustrated in FIGS. 2, 3 and 4. FIG. 2 shows liquid fluid 12a draining down through first receiving channel 42b and entering first storage compartment 42a via first passageway 92. Solid body matter 14, typically denser than liquid fluid 12a, falls out of solution and settles at the bottom of the first-stage fluid collection chamber 42, so flow paths downstream of first passageway 92 do not have to contend with such potential flow obstructions. Suction source 50 extracts gaseous fluid 12b through passageways 112 and 113 and through fluidic seal 38. As collected liquid fluid 12a rises within first storage compartment 42a, first vent 102 releases otherwise trapped gaseous fluid 12b within first storage compartment 42a to overflow chamber 44. Thus, first vent 102 helps equilibrate the liquid levels in first receiving channel 42b and first storage compartment 42a.

In FIG. 3, after first-stage fluid collection chamber 42 fills with liquid fluid 12a, additional overflowing liquid fluid 12a flows across first lid 80, through first interstage spillway 98, down into second receiving channel 46b, through second passageway 94 and up through second storage compartment 46a. As collected liquid fluid 12a rises within second storage compartment 46a, second vent 104 releases otherwise trapped gaseous fluid 12b within second storage compartment 46a to overflow chamber 44. Thus, second vent 104 helps equilibrate the liquid levels in second receiving channel 46b and second storage compartment 46a.

In FIG. 4, after second-stage fluid collection chamber 46 fills with liquid fluid 12a, additional overflowing liquid fluid 12a flows across second lid 82, through second interstage spillway 100, down into third receiving channel 48b, through third passageway 96 and up through third storage compartment 48a. As collected liquid fluid 12a rises within third storage compartment 48a, third vent 106 releases otherwise trapped gaseous fluid 12b within third storage compartment 48a to overflow chamber 44. Thus, third vent 106 helps equilibrate the liquid levels in third receiving channel 48b and third storage compartment 48a. After third-stage fluid collection chamber 48 fills with liquid fluid 12a, additional liquid 12a can be collected in overflow chamber 44, which is the area above lids 80, 82 and 84.

Still referring to FIG. 4, although the specific design of suction regulator 34 and fluidic seal 38 may vary, suction regulator 34, in the illustrated example, comprises a manometer or U-tube with a first leg 34a of the U-tube containing water 32 at an upper level 116 and a second leg 34b of the U-tube containing the same water at a lower level 118. An opening 122 connects the lower ends of the two legs 34a and 34b in fluid communication with each other. The upper end of first leg 34a is open to suction source 50, and the upper end of second leg 34b via a vent 117 is open to ambient air at atmospheric pressure. Consequently, the absolute air pressure above upper level 116 substantially equals the water head pressure differential between the upper and lower levels 116 and 118. If suction source 50 extracts more air than is needed to maintain the desired predetermined subatmospheric pressure in suction regulator 34, atmospheric air within second leg 34b bubbles up into first leg 34a, as indicated by air bubbles 124.

In the illustrated example, a baffle 126 connects suction regulator 34 in fluid communication with a first side 128 or first water level of fluidic seal 38. Via valve 22 and passageways 112 and 113, a second side 134 or second water level of fluidic seal 38 is exposed to air (gaseous fluid 12b) in fluid collection chambers 42, 46 and 48. In the illustrated example, fluidic seal 38 comprises a manometer or U-tube with one leg 136 containing sealing water 36 at first water level 128 and another leg 138 containing sealing water 36 at second water level 134. A lower passageway 140 connects the two legs of the U-tube. When water levels 128 and 134 are at the same elevation, the absolute air or gas pressure in fluid collection chambers 42, 46 and 48 generally equals the controlled subatmospheric pressure in suction regulator 34. A difference in elevation of levels 128 and 134 indicates that the absolute pressure of gas or air in fluid collection chambers 42, 46 and 48 and overflow chamber 44 deviates from the controlled subatmospheric pressure in control section 34, which can happen for various reasons.

For instance, fluid 12a in a liquid state draining into container 10 via chest tube 18 increases the total volume of fluid 12 (gas 12b and liquid 12a) in fluid collection chambers 42, 46 and 48, so the absolute pressure in those chambers increases, which lowers water level 134. In other words, liquid 12a draining from patient 16 into container 10 displaces air (fluid 12b) in fluid collection chambers 42, 46 and 48 and pushes water level 134 down accordingly. The displaced air (fluid 12b), at times, pushes water level 134 down so far that the displaced air bubbles up through visual bubble indicator 52 in the left leg 136 of the manometer. Such bubbling, caused by body fluid 12b entering container 10, is usually quite slow and sometimes barely noticeable because the volume of the bubbles should generally equal the volume the incoming body fluids 12, wherein the liquid portion 12a of fluid 12 commonly flows only at about 1 to 3 cc/hr (of course sometimes more, sometimes less). If an average bubble is 5 mm in diameter, a liquid flow rate of 2 cc/hr converts to about one bubble every two minutes. The relevance of this can be quite important as it relates to the present invention because the volume flow of body liquids 12a and gas 12b through chest drainage container 10 is a driving factor in strategically sizing vents, spillways and other flow passageways.

It should be noted that although excessive bubbling can indicate a high volume of body liquids 12a entering container 10, it really often indicates an air leak exists where chest tube 18 connects to patient 16. Thus, bubble indicator 52 is often relied upon as a visual warning of an air leak. It should also be noted that a patient's normal breathing process can create fluctuating subatmospheric air pressure in fluid collection chambers 42, 46 and 48 and overflow chamber 44, which in turn causes modest undulating or "tidaling" in the fluidic seal's second level 134.

Sometimes, however, a patient's abnormal or interrupted breathing process creates excessively low and prolonged subatmospheric pressure in fluid collection chambers 42, 46 and 48 and overflow chamber 44. This can cause the fluidic seal's second level 134 to rise to a point where water 36 totally fills the manometer's right leg 138 up to and beyond float valve 22. To prevent the water column from being freely blown up and out of the manometer's right leg 138, and thereby breaking the integrity of fluidic seal 38, float 28 floats atop the water column in leg 138 to engage valve seat 26. Float 28 engaging valve seat 26 then advantageously restricts the water's upward flow through the valve's controlled leak path 24. In some examples, leak path 24 is a notch in valve seat 26 and is sized to delay the completion of the "blow out" process. This is explained further in Teleflex's U.S. Pat. No. 5,507,734. Float valve 22 is being described here because it plays a role in preventing undesirable inter-chamber mixing of collected body liquid during a tip-over condition.

Figure 5:
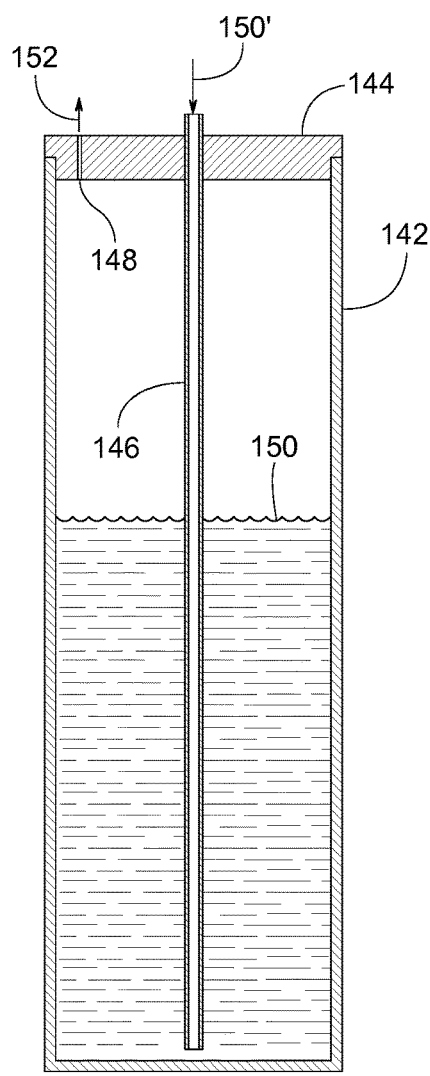
FIG. 5 is a schematic diagram of a model illustrating an operating principle pertaining to the chest drainage container.

FIGS. 5-8 schematically illustrate the chest drainage container's basic principle of fluid containment during a tip-over event. The illustrated model is a bottle 142 with a cap 144, a straw 146 and a breather hole 148 in cap 144. This example is similar to a conventional drinking bottle, but with a straw leading to the bottom of the bottle. FIG. 5 shows a liquid 150 can freely flow down into the straw 146 as a tiny breather hole 148 readily releases displaced air 152 above the liquid level within bottle 142.

Figure 6:
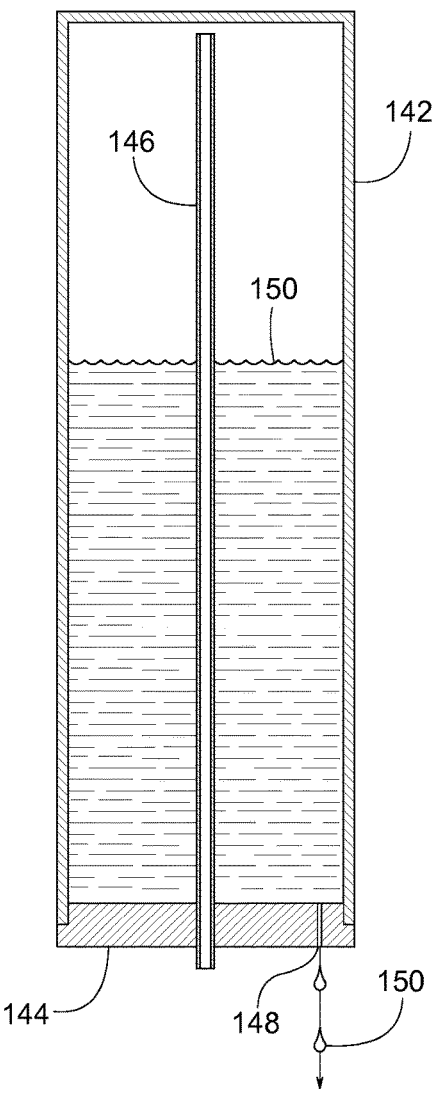
FIG. 6 is a schematic diagram similar to FIG. 5 but showing the model completely inverted.

When bottle 142 is fully inverted, as shown in FIG. 6, or partially inverted as shown in FIGS. 7 and 8, liquid 150 can only dribble out because breather hole 148 is about 30 times more restrictive to liquid flow than to airflow. More specifically, for a given vent or orifice diameter conveying fluid under conditions typical of a chest drainage container, the vent would generally convey the fluid at a volumetric flow rate that is about 30 times slower for water than for air.

In the model shown in FIGS. 5-8, bottle 142 can represent second fluid collection chamber 46, straw 146 represents second receiving channel 46b, cap 144 represents second lid 82, and breather hole 148 represents second vent 104. The annular volume between the exterior of straw 146 and the interior of bottle 142 can represent second storage compartment 46a. Arrow 150' can represent liquid body fluid 12a flowing through first spillway 98 into second receiving channel 46b, and arrow 152 can represent air or gaseous body fluid 12b passing through second vent 104 into overflow chamber 44 (overflow chamber 44 not shown represented in the model).

Figure 10:
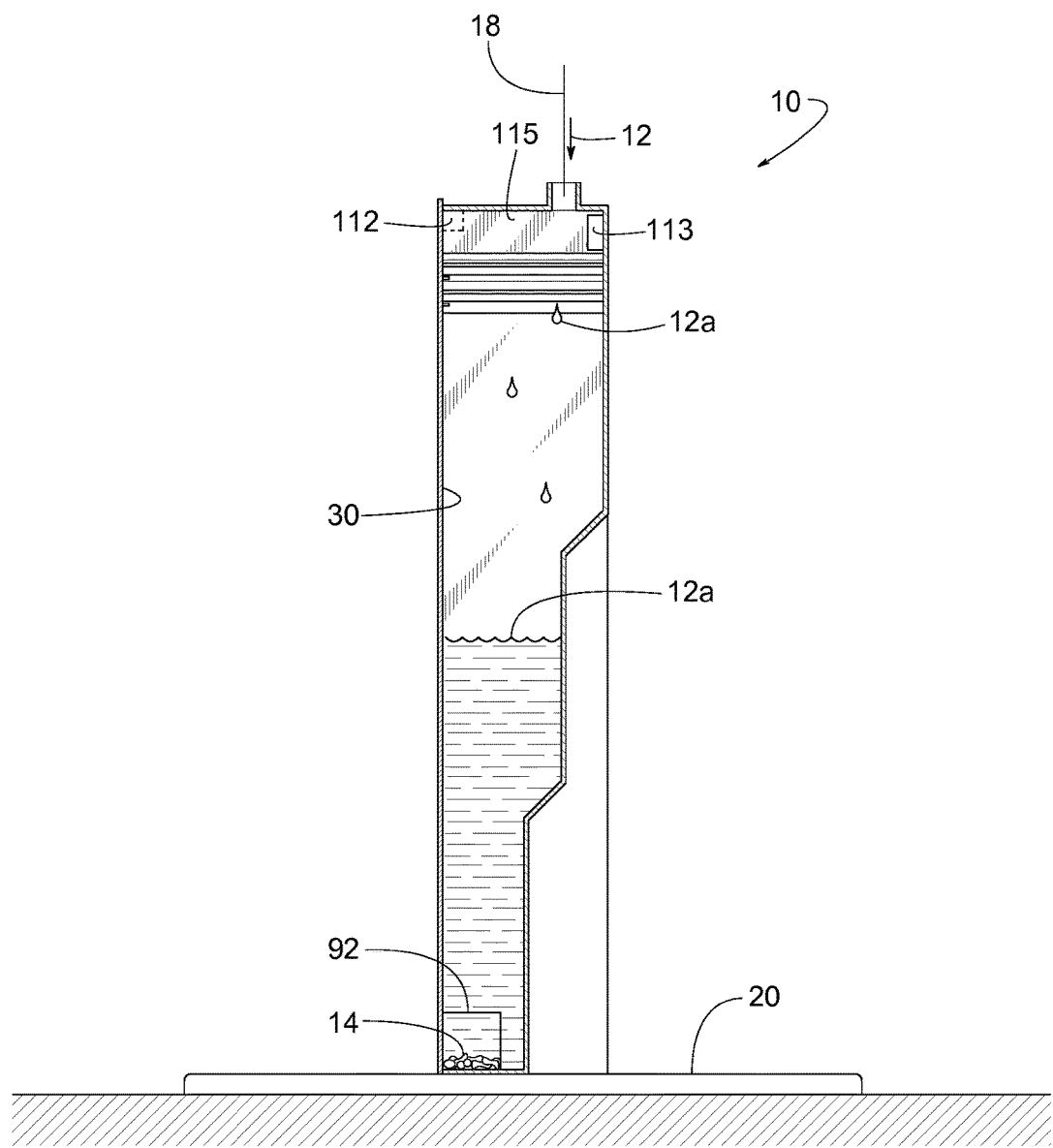
FIG. 10 is a cross-sectional view taken along 10-10 of FIG. 2.
Figure 13:
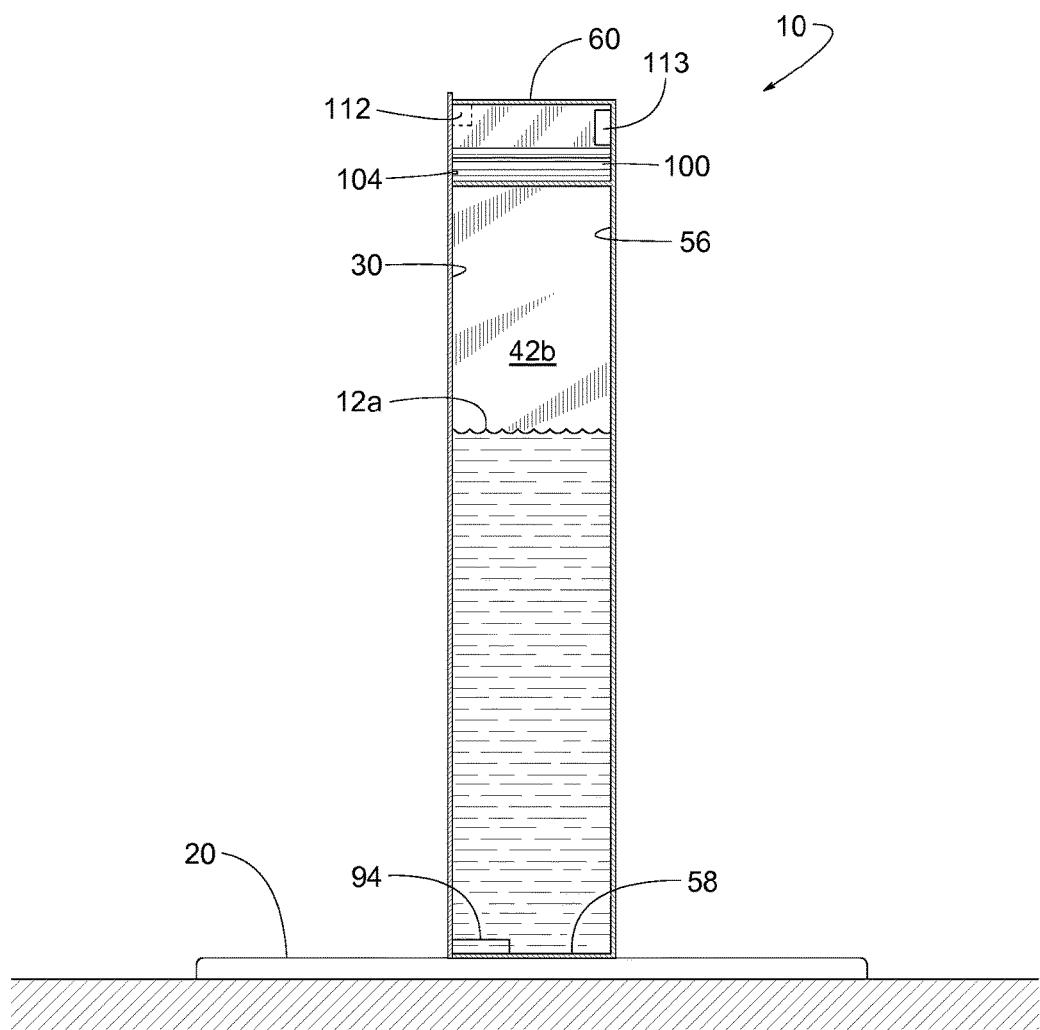
FIG. 13 is a cross-sectional view taken along line 13-13 of FIG. 3.
Figure 14:
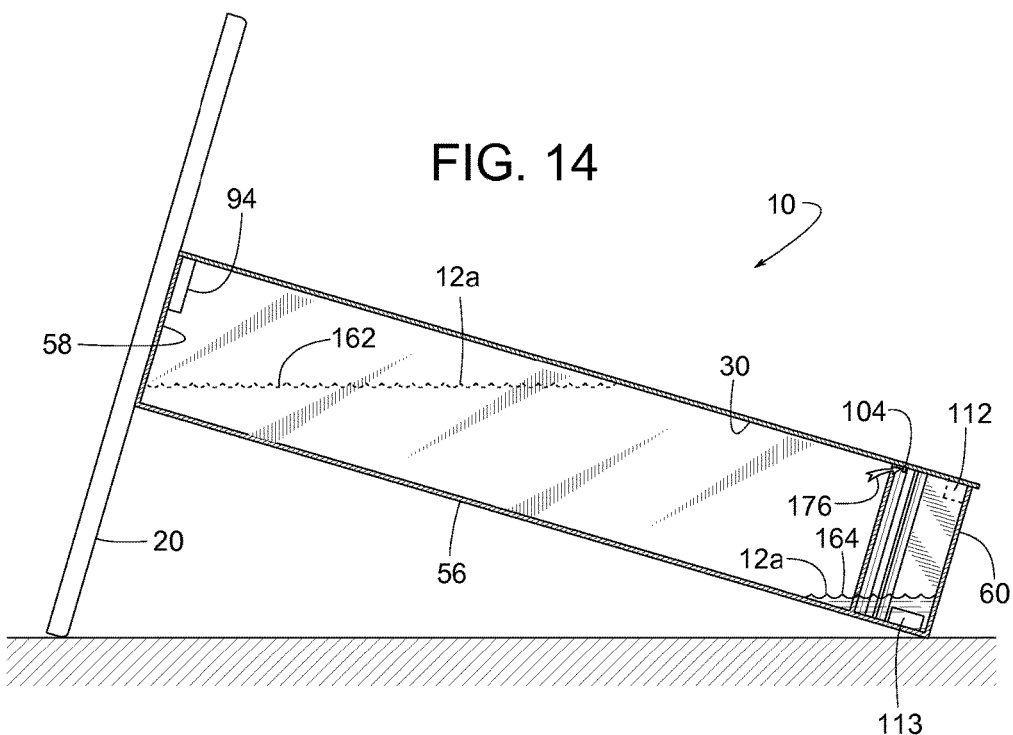
FIG. 14 is a cross-sectional view similar to FIG. 13 but showing the chest drainage container tipped over to the reclined position.
Figure 15:
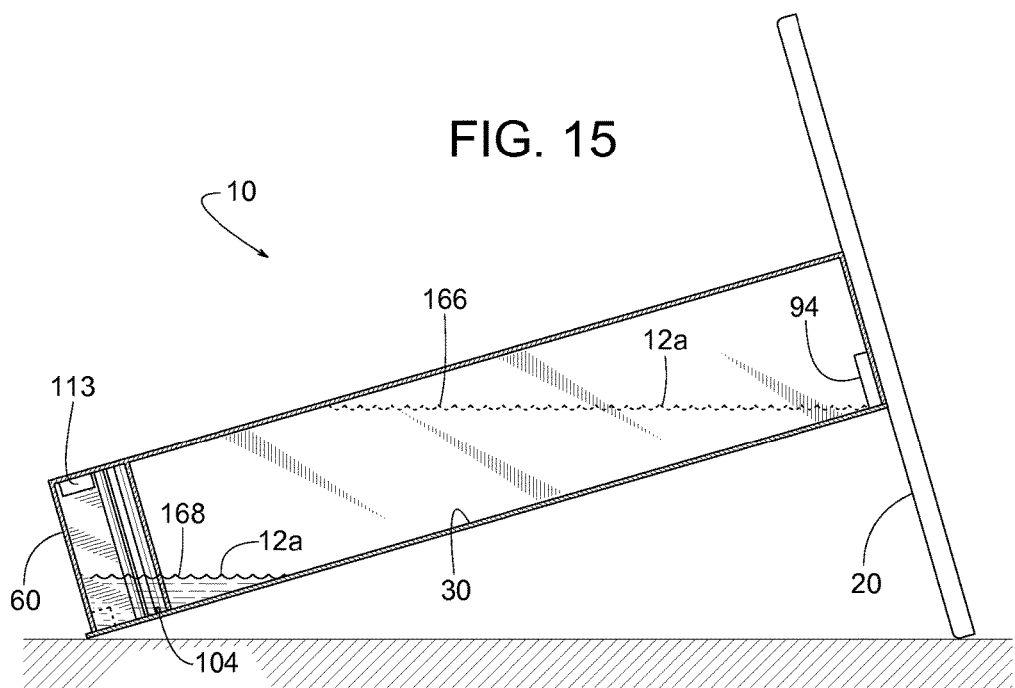
FIG. 15 is a cross-sectional view similar to FIG. 13 but showing the chest drainage container tipped over to the prostrate position.

FIGS. 9-15 show how chest drainage container 10 takes full advantage of the principle illustrated in FIGS. 5-8. FIGS. 9, 10 and 13 show chest drainage container 10 in an upright position. The term, "upright position" refers to the chest drainage container's normal operating position, which is not necessarily perfectly vertical. In some examples, the chest drainage container in its upright or normal operating position is leaning slightly back for stability. FIGS. 11 and 14 show chest drainage container 10 tipped back to a reclined position with front panel 30 facing generally up. Front panel 30 facing generally up does not necessarily mean that front panel 30 is horizontal and facing straight up, rather it means that front panel 30 is facing more upward during the reclined position than during the upright position. FIGS. 12 and 15 show chest drainage container 10 tipped forward to a prostrate position with front panel 30 facing generally down. Front panel 30 facing generally down does not necessarily mean that front panel 30 is horizontal and facing straight down, rather it means that front panel 30 is facing more downward in the prostrate position than during the upright position.

Chest drainage containers can be accidentally knocked over by someone inadvertently kicking or bumping the container from the front, in which case the container would be more likely to fall back than forward. It has been discovered, however, that tubes (e.g., tube 18) draped across the patient's body and leading to the chest drainage container can be inadvertently snagged or pulled, which can pull the container forward to where the container tips over to its prostrate position. Chest drainage containers that are set on the floor are often backed up against the bed or other furniture in the room, thus a chest drainage container might be more likely to fall forward than back. Consequently, the present invention includes features that provide a chest drainage container with tolerance for tipping in either direction.

FIG. 9 shows chest drainage container 10 in its upright position with first storage compartment 42a and first receiving channel 42a empty. FIG. 10 shows chest drainage container 10 in its upright position with first storage compartment 42a and first receiving channel 42b about half full of liquid fluid 12a. When chest drainage container 10 is accidentally tipped back to its reclined position, shown in FIG. 11, most of liquid fluid 12a collected in first storage compartment 42a stays trapped within compartment 42a and settles to liquid level 154 while a limited portion of liquid fluid 12a might escape back through first passageway 92 and dribble out through first vent 102. Since first receiving channel 42b is significantly smaller than first storage compartment 42a, a relatively small volume of liquid fluid 12a collected in first receiving channel 42b settles to liquid level 156 while the remaining portion of the first receiving channel's liquid flows into overflow chamber 44. When chest drainage container 10 is returned to its upright position, lids 80, 82 and 84 direct the overflow liquid 12a back into first receiving channel 42b to return chest drainage container 10 to normal operation.

When chest drainage container 10 is accidentally tipped forward to its prostrate position, shown in FIG. 12, most of liquid fluid 12a collected in first storage compartment 42a stays trapped within compartment 42a and settles to liquid level 158 while a limited portion of liquid fluid 12a might escape back through first passageway 92 and dribble out through first vent 106. Since first receiving channel 42b is significantly smaller than first storage compartment 42a, a relatively small volume of liquid fluid 12a collected in first receiving channel 42b settles to liquid level 160 while the remaining portion of the first receiving channel's liquid flows into overflow chamber 44. When chest drainage container 10 is returned to its upright position, lids 80, 82 and 84 direct the overflow liquid 12a back into first receiving channel 42b to return chest drainage container 10 to normal operation.

FIG. 13 shows chest drainage container 10 in its upright position with second storage compartment 46a and second receiving channel 46b about half full of liquid fluid 12a. When chest drainage container 10 is accidentally tipped back to its reclined position, shown in FIG. 14, most of liquid fluid 12a collected in second storage compartment 46a stays trapped within compartment 46a and settles to liquid level 162 while a limited portion of liquid fluid 12a might escape back through second passageway 94 and dribble out through second vent 104. Since second receiving channel 46b is significantly smaller than second storage compartment 46a, a relatively small volume of liquid fluid 12a collected in second receiving channel 46b settles to liquid level 164 while the remaining portion of the second receiving channel's liquid flows into overflow chamber 44. When chest drainage container 10 is returned to its upright position, lids 80, 82 and 84 direct the overflow liquid 12a back into the first and second receiving channels 42b and 46b to return chest drainage container 10 to normal operation.

When chest drainage container 10 is accidentally tipped forward to its prostrate position, shown in FIG. 15, most of liquid fluid 12a collected in second storage compartment 46a stays trapped within compartment 46a and settles to liquid level 166 while a limited portion of liquid fluid 12a might escape back through second passageway 94 and dribble out through second vent 104. Since second receiving channel 46b is significantly smaller than second storage compartment 46a, a relatively small volume of liquid fluid 12a collected in second receiving channel 46b settles to liquid level 168 while the remaining portion of the second receiving channel's liquid flows into overflow chamber 44. When chest drainage container 10 is returned to its upright position, lids 80, 82 and 84 direct the overflow liquid 12a back into the first and second receiving channels 42b and 46b to return chest drainage container 10 to normal operation. The tip-over response of third-stage fluid collection chamber 48 is similar to that of the first and second-stage fluid collection chambers 42 and 46.

Considering the fluid containment principle illustrated in FIGS. 5-8 in view of the chest drainage container's functional requirements described with reference to FIGS. 2-4, some examples of the container's various vents, passageways and spillways are positioned and sized according to one or more of the following:

(1) In some examples, the horizontal cross-sectional area of first receiving channel 42b is larger than the opening through main fluid inlet 108. This ensures that any fluid 12 that can pass through chest tube 18 can also flow down through first receiving channel 42b.

(2) In some examples, the vertical cross-sectional area of overflow chamber 44 is wide open to ensure that the main fluid inlet 108 is kept fully exposed to the desired suction pressure.

(3) In some examples, the volume of each receiving channel 42b, 46b and 48b is appreciably smaller than its respective storage compartment 42a, 46a and 48a to maximize the containment of liquid fluid 12a within compartments 42a, 46a and 48a during a tip-over incident.

(4) In some examples, the horizontal cross-sectional areas of receiving channels 46b and 48b are smaller than that of first receiving channel 42b as only the first receiving channel 42b might need to convey tissue and clots.

(5) In some examples, passageways 94 and 96 are smaller than first passageway 92 because only the first passageway 92 might need to convey tissue and clots.

(6) In some examples, the openings through interstage spillways 98 and 100 are rather small because during normal operation they only have to convey fluid 12 in one direction, as opposed prior designs where liquid enters while gas exits through the same opening. As liquid fluid 12a enters through spillways 98 and 100, gas fluid 12b exits through vents 104 and 106 for unidirectional flow. Moreover, tissue and clots fall out of solution and collect at the bottom of first receiving channel 42b prior to liquid fluid 12a reaching spillways 98 and 100, so the spillways do have to be oversized for conveying tissue and clots.

(7) In some examples, the openings through interstage spillways 98 and 100 can be minimized to convey only liquid fluid 12a because voluminous gaseous fluid 12b bypasses the spillways by flowing directly through the wide open overflow chamber 44 from the container's main inlet 108, through passageways 112 and 113, to fluidic seal 38.

(8) Upon righting a tipped over chest drainage container 10, to ensure liquid fluid 12a in overflow chamber 44 returns to the proper fluid collection chambers, in some examples, lid 84 overlaps lid 82, and lid 82 overlaps lid 80.

(9) In some examples, to minimize liquid fluid 12a from draining out through a vent when container 10 is tipped over, the vent has a vent flow coefficient that is less than a passageway flow coefficient of a passageway associated with the vent. For example, first passageway 92 has a passageway flow coefficient that is greater than the vent flow coefficient of first vent 102, second passageway 94 has a passageway flow coefficient that is greater than the vent flow coefficient of second vent 104, and/or third passageway 96 has a passageway flow coefficient that is greater than the vent flow coefficient of third vent 106. A passageway having a greater flow coefficient than a vent means that the vent is more of a flow restriction than the passageway, e.g., for a given liquid and delta pressure through the opening, the vent provides greater flow resistance than the passageway. The term, "flow coefficient" (regardless of the fluid, e.g., fluid 12a or 12b) is defined herein as being equal to the volume (in US gallons) of water at 60 degrees Fahrenheit that will flow per minute through the specified opening with a pressure drop of one psi across the opening.

(10) In some examples, to minimize liquid fluid 12a from draining out through a vent when container 10 is tipped over, the vent has a vent flow coefficient that is less than a receiving flow coefficient of a receiving channel inlet. For example, receiving channel inlet 114 has a receiving flow coefficient that is greater than the vent flow coefficient of first vent 102, first spillway 98 has a receiving flow coefficient that is greater than the vent flow coefficient of second vent 104, and/or second spillway 100 has a receiving flow coefficient that is greater than the vent flow coefficient of third vent 106. A receiving channel inlet having a greater flow coefficient than a vent means that the vent is more of a flow restriction than the receiving channel inlet, e.g., for a given liquid and delta pressure through the opening, the vent provides greater flow resistance than the receiving channel inlet.

(11) In some examples, to minimize liquid fluid 12a from draining out through a vent when container 10 is tipped over, the vent has a vent flow coefficient that is less than a spillway flow coefficient of a spillway associated with the vent. For example, first spillway 98 has a first spillway flow coefficient that is greater than a second vent flow coefficient of second vent 104, and/or second spillway 100 has a second spillway flow coefficient that is greater than a third vent flow coefficient of third vent 106. A spillway having a greater flow coefficient than a vent means that the vent is more of a flow restriction than the spillway, e.g., for a given liquid and delta pressure through the opening, the vent provides greater flow resistance than the spillway.

(12) In some examples, to prevent liquid fluid 12a from flowing into fluidic seal 38 during a tip-over condition, overflow chamber 44 is larger in volume than receiving channel 42b, 46b and/or 48b.

(13) In some examples, vents 102, 104 and 106 are small slots or notches that are open to front panel 30 so that the vents can be integrally formed while plastic injection molding the container's main body. FIG. 16, for example, shows third vent 106 being open in an area 168 immediately adjacent front panel 30. In some examples, as shown in FIG. 16A, the third vent is a horizontally elongate slit 106' or narrow gap defined by a tapered knife edge 170 being slightly spaced apart from front panel 30. The spaced apart knife edge 170 avoids being ultrasonically welded to front panel 30 and minimizes being seen through an upper portion of a graduated window 172 (FIG. 19).

(14) In some examples, passageways 92, 94 and 96 are slots, notches or other voids that are open to front panel 30 so that the passageways can be integrally formed while plastic injection molding the container's main body.

(15) In some examples, spillways 98 and 100 are voids that are open to front panel 30 so that the spillways can be integrally formed while plastic injection molding the container's main body.

(16) In some examples, lids 80, 82 and/or 84 are closer to top panel 60 than to bottom panel 58 to maximize the storage volume of fluid collection chambers 42, 46 and 48.

(17) To minimize the volumes of receiving channels 46b and 48b and thus minimize the volume of liquid fluid 12a they might release during a tip-over event, some examples of container 10 have smaller receiving channels 46b' and 48b' by virtue of having less front-to-back depth, as shown in FIG. 17A.

(18) In some examples, vents 102, 104 and 106 have an opening area of about one to four square millimeters to provide sufficient venting of gas 12b during normal operation and sufficient flow restriction of liquid 12a during a tip-over condition.

Liquid and gas flow through chest drainage container 10, at times, can be as described with reference to the example shown in FIGS. 3 and 14. The condition shown in FIG. 3 is during a first period, and the condition shown in FIG. 14 is during a second period. In this example, FIG. 3 shows a first current of fluid 174 flowing at a first volumetric flow rate through second passageway 94, wherein the first volumetric flow rate may vary. FIG. 3 also shows a second current of fluid 176 flowing at a second volumetric flow rate through second vent 104, wherein the second volumetric flow rate may vary as well.

During the first period, illustrated in FIG. 3, the first volumetric flow rate on average is substantially equal to the second volumetric flow rate (with the exception of incidental differential pressure fluctuations). For a given pressure differential across second vent 104, the second volumetric flow rate during the second period (FIG. 14) is appreciably less than the second volumetric flow rate during the first period (FIG. 3).

Figure 18:
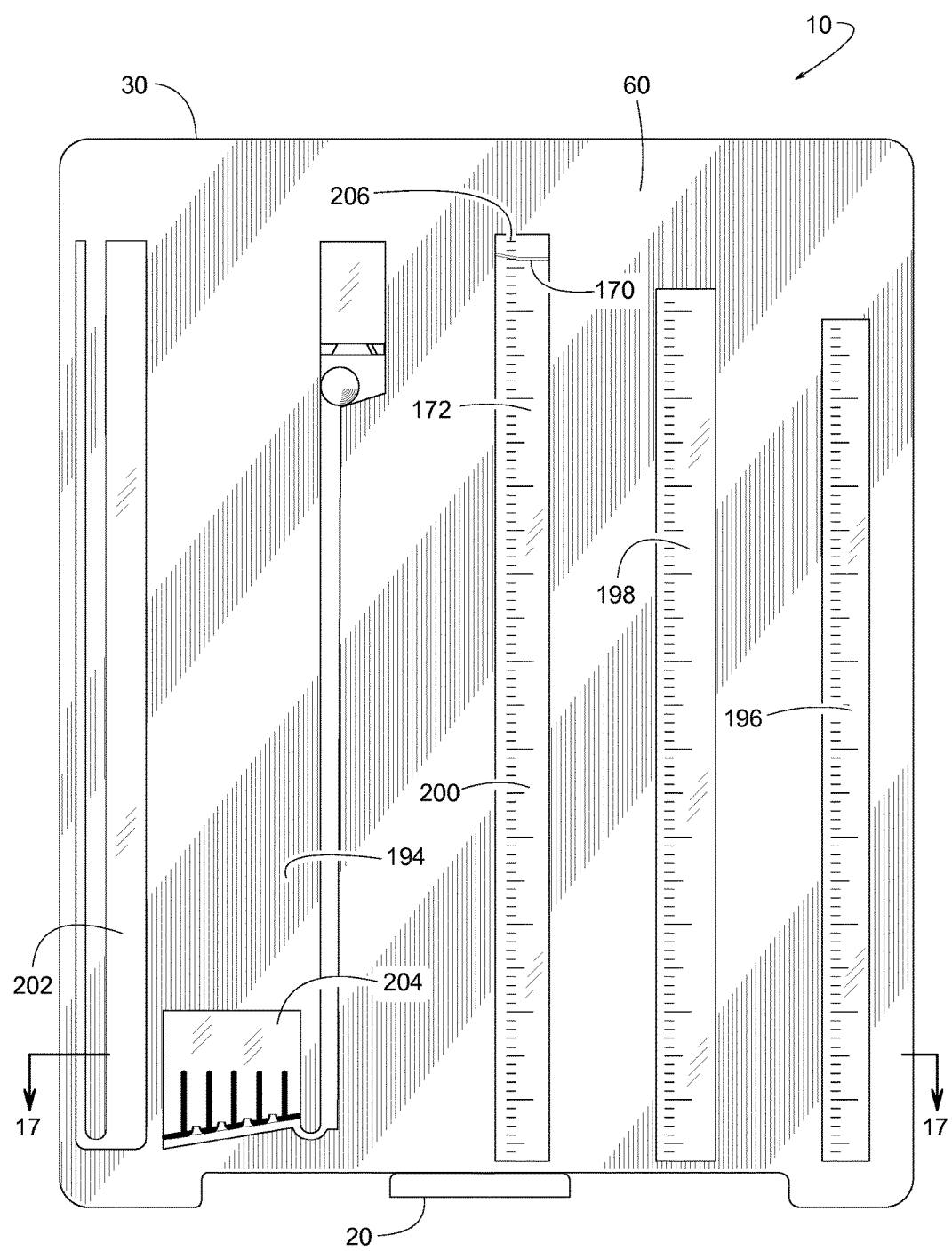
FIG. 18 is a front view similar to FIG. 1 but showing more of the container's front panel.

FIG. 18 shows front panel 30 ultrasonically welded, bonded or otherwise sealed and attached to the main body of chest drainage container 10. Some examples of front panel 30 have a graphic overlay 194 with see-through windows for observing certain areas within chest drainage container 10. In the illustrated example, for instance, front panel 30 has graduated windows 196, 198 and 200 for observing the liquid levels in storage compartments 42a, 46a and 48a, respectively. In some examples, the graduations of windows 196, 198 and 200 are on the windows. In some examples, the graduations of windows 196, 198 and 200 are on the graphic overlay adjacent to the windows. The illustrated example of front panel 30 also includes a window 202 for observing suction regulator 34 and another window 204 for observing fluidic seal 38. In some examples, graduated window 200 identifies an uppermost fill level 206 that is higher than storage compartment 48a and displays some portion of overflow chamber 44 when chest drainage container 10 is in the upright position.

In some examples, a graduated window places a storage compartment in view while and an adjacent area of graphic overlay 194 covers the storage compartment's associated receiving channel. This makes it easier, in the presence of incidental pressure fluctuations, to accurately measure the liquid level in a fluid collection chamber because a storage compartment will have a more stable liquid level than that of its associated receiving channel due to their relative horizontal cross-sectional areas. In other words, the window looks at the slower moving leg of the manometer.

In some examples that include foot 20 attached to a main body of chest drainage container 10, foot 20 assumes various orientations, such as a normal operating position (shown in FIGS. 1-4, 9, 10, 13 and 19), a tipped back position (shown in FIGS. 11 and 14), and a tipped forward position (shown in FIGS. 12 and 15). Foot 20 in the tipped back position points front panel 30 upward and stabilizes chest drainage container 10 in the reclined position. Foot 20 in the tipped forward position points front panel 30 downward and stabilizes container 10 in the prostrate position. Foot 20 in the normal operating position stabilizes chest drainage container 10 in the upright position with top panel 60 being above bottom panel 58 and with vent 102, 104 and/or 106 being above passageway 92, 94 and/or 96. When chest drainage container 10 is tipped over with foot 20 being in the tipped back or tipped forward position, vent 102, 104 and/or 106 is lower than passageway 92, 94 and/or 96 to take advantage of the principle illustrated in FIGS. 5-8.

Although the invention is described with respect to a preferred embodiment, modifications thereto will be apparent to those of ordinary skill in the art. The scope of the invention, therefore, is to be determined by reference to the following claims:

The invention claimed is:

1. A chest drainage container for collecting a fluid from a chest cavity of a patient, the chest drainage container having selectively an upright position, a reclined position, and a prostrate position, the chest drainage container comprising:
    a back panel;
    a bottom panel extending from the back panel, the bottom panel being horizontally elongate when the chest drainage container is in the upright position;
    a top panel extending from the back panel, the top panel being horizontally elongate when the chest drainage container is in the upright position, the top panel being higher than the bottom panel when the chest drainage container is in the upright position;
    a first outer side wall extending from the back panel and extending between the top panel and the bottom panel, the first outer side wall being vertically elongate when the chest drainage container is in the upright position;
    a second outer side wall extending from the back panel and extending between the top panel and the bottom panel, the second outer side wall being vertically elongate when the chest drainage container is in the upright position;
    a main body comprising the back panel, the bottom panel, the top panel, the first outer side wall and the second outer side wall;
    a front panel attached to the main body, the front panel spanning a width and a height of the main body, the front panel and the back panel defining a front-to-back depth therebetween, the front panel being inclined and facing generally up when the chest drainage container is in the reclined position, the front panel being inclined and facing generally down when the chest drainage container is in the prostrate position;
    a dividing wall extending between the back panel and the front panel, the dividing wall being offset from the first outer side wall to define a fluid collection chamber between the first outer side wall and the dividing wall, the fluid collection chamber being vertically elongate when the chest drainage container is in the upright position, the dividing wall extending from the bottom panel toward the top panel, the dividing wall having an upper end that is closer to the top panel than to the bottom panel;
    a partition extending between the back panel and the front panel, the partition being between the first outer side wall and the dividing wall, the partition being vertically elongate when the chest drainage container is in the upright position, the partition dividing the fluid collection chamber into a storage compartment and a receiving channel, the chest drainage container defining a passageway that is closer to the bottom panel than to the top panel, the passageway connecting the receiving channel in fluid communication with the storage compartment;
    a lid underneath and spaced apart from the top panel and extending over the storage compartment when the chest drainage container is in the upright position, the lid being closer to the top panel than to the bottom panel;
    an overflow chamber being between and defined by the top panel and the lid;
    a vent proximate the lid and being defined by at least one of the lid, the partition and the dividing wall, the vent providing fluid communication between the storage compartment and the overflow chamber, the vent having a vent flow coefficient; and
    a receiving channel inlet defined by at least one of the first outer wall, the dividing wall and the partition, the receiving channel inlet connecting the receiving channel in fluid communication with a main fluid inlet defined by at least one of the main body and the front panel, the receiving channel inlet having a receiving flow coefficient that is greater than the vent flow coefficient.

2. The chest drainage container of claim 1, wherein the storage compartment is larger in volume than the receiving channel.

3. The chest drainage container of claim 1, wherein the passageway has a passageway flow coefficient that is greater than the vent flow coefficient.

4. The chest drainage container of claim 1, wherein the back panel, the bottom panel, the top panel, the first outer side wall, the second outer side wall, the dividing wall and the partition together comprise a seamless unitary piece.

5. The chest drainage container of claim 1, wherein the front panel has a graduated window identifying an uppermost fill level that is higher than the storage compartment when the chest drainage container is in the upright position.

6. The chest drainage container of claim 1, wherein the overflow chamber is larger in volume than the receiving channel.

7. The chest drainage container of claim 1, further comprising a fluidic seal interposed between the back panel and the front panel, the fluidic seal comprising a valve seat and a float, the valve seat defining a leak path between the float and the valve seat when the float engages the valve seat.

8. The chest drainage container of claim 1, further comprising a foot attached to the main body, the foot having selectively a normal operating position, a tipped back position and a tipped forward position, the foot in the tipped back position points the front panel upward, the foot in the tipped forward position points the front panel downward, the foot in the normal operating position stabilizes the chest drainage container in the upright position with the top panel being above the bottom panel, the vent being above the passageway when the chest drainage container is in the upright position, and the vent being lower than the passageway when the foot is in at least one of the tipped back position and the tipped forward position.

* * * * *